United States Patent [19]
Heimke et al.

[11] Patent Number: 5,370,698
[45] Date of Patent: Dec. 6, 1994

[54] ISOELASTIC IMPLANTS WITH IMPROVED ANCHORAGE MEANS

[75] Inventors: Gunther Heimke, Clemson; Andreas F. Von Recum, Six Mile, both of S.C.

[73] Assignee: Clemson University, Clemson, S.C.

[21] Appl. No.: 63,639

[22] Filed: May 18, 1993

Related U.S. Application Data

[63] Continuation of Ser. No. 870,493, Apr. 16, 1992, abandoned.

[51] Int. Cl.⁵ ............................. A61F 2/30; A61F 2/32
[52] U.S. Cl. ........................................ 623/18; 623/23; 623/22
[58] Field of Search ................... 603/16, 17, 18, 19, 603/22, 23

[56] References Cited

U.S. PATENT DOCUMENTS

| | | | |
|---|---|---|---|
| 3,314,420 | 4/1967 | Smith et al. | |
| 3,605,123 | 9/1971 | Hahn . | |
| 3,806,957 | 4/1974 | Shersher . | |
| 3,808,606 | 5/1974 | Tronzo | 623/22 |
| 4,052,754 | 10/1977 | Homsy | 623/16 |
| 4,179,485 | 12/1979 | Tritten . | |
| 4,330,514 | 5/1982 | Nagai et al. | |
| 4,373,217 | 2/1983 | Draenert . | |
| 4,406,023 | 9/1983 | Harris . | |
| 4,430,761 | 2/1984 | Niederer et al. | 623/23 |
| 4,566,138 | 1/1986 | Lewis et al. | 623/22 |
| 4,599,085 | 7/1986 | Russ et al. | 423/28 |
| 4,642,124 | 2/1987 | Cooke . | |
| 4,704,127 | 11/1987 | Averill et al. | 623/22 |
| 4,718,912 | 1/1988 | Crowninshield . | |
| 4,795,472 | 1/1989 | Crowninshield | 623/28 |
| 4,828,565 | 5/1989 | Duthoit et al. | 623/22 |
| 4,878,919 | 11/1989 | Pavlansky et al. | 623/23 |
| 4,904,263 | 2/1990 | Buechel et al. | 623/23 |
| 5,002,580 | 3/1991 | Noble et al. | 623/23 |
| 5,116,380 | 5/1992 | Hewka et al. | 623/23 |
| 5,176,712 | 1/1993 | Homsy | 623/23 |

*Primary Examiner*—David Isabella
*Attorney, Agent, or Firm*—Dority & Manning

[57] ABSTRACT

Isoelastic implants are provided with a surface roughness for anchorage in and load transmission to the surrounding tissue. The surface roughness is formed of one or more of the structures including undulations, or grooves, or pores, or lacunae, or gaps and protrusions. The roughness is located at two separate and confined regions along the surfaces of the implant which are intended for transmitting loads from the surrounding tissue into the implant or vice versa. The regions for containing the roughness are confined to two small areas at the opposite ends of the implant's surface. The ends are defined in relation to the direction of the load to be transmitted through the surfaces.

16 Claims, 7 Drawing Sheets

ISOELASTIC IMPLANTS WITH IMPROVED ANCHORAGE MEANS

This a continuation of application Ser. No. 07/870,493, filed Apr. 16, 1992, which was abandoned upon the filing hereof.

BACKGROUND OF THE INVENTION

The present invention relates to man-made implants which replace bones in mammals and more particularly to implants which replace major load bearing sections of bones.

Towards the end of the nineteen-sixties it had been realized that the survival rates of implants anchored via a layer of polymethylmethacrylate bone cement will be limited by the inherent properties of this so called PMMA. During the nineteen-seventies, the search for other modes of implant fixation led to new implant systems. In the United States, several types of porous structures found widespread applications.

The much improved long term success rates of these and other implant systems, in particular of bone and joint replacements, have lead to a reevaluation of the modes of failure:

1. All metal implants are much stiffer than the tissues they replace. This mechanical mismatch has long been considered to contribute significantly to incomplete integration of implants with the surrounding bone tissue. The disuse atrophy observed around many implant systems is regarded as one of the major results of these discontinuities.
2. The necessity for the consideration of systemic effects of metals which previously had been regarded as sufficiently biocompatible has been realized recently from statistical evaluations based on nationwide cancer record systems in New Zealand and Finland. Studies of tissue samples from the vicinity of retrieved titanium alloy implants presented at the Orthopaedic Research Society and the American Academy of Orthopaedic Surgeons Conferences in New Orleans, La. in February 1991 showed that even this titanium alloy does stimulate reactions not much more favorable than those observed around implants made of the cobalt-based alloys.

To overcome the first of these difficulties, the use of isoelastic implants had already been proposed more than ten years ago. As polymers only can match the elastic properties of bone and other kinds of tissue, but do not provide the mechanical strength necessary for load bearing implants, different kinds of fiber reinforcements have been studied in much detail during the last decade in the United States and other countries. Now, with the realization of the systemic effects of long term metallic implants, these polymer implants gain a much higher importance than intended originally. Some may regard them as the last hope for a reliable further extension of implant survival rates. But the success rates of the previous isoelastic implants have remained unconvincingly low.

Most permanent, load bearing implants have a much higher stiffness than the tissue they replace or to which they are intended to transmit loads. This is particularly true for the anchorage portions of joint replacements in the lower extremities. The necessity to reliably stabilize such implants in the bony structures adjacent to the joints which actually need replacement, demands relatively linearly extended anchorage portions. In many cases, the load transfer from the bony tissue to the implant is confined to only small portions of the interface between the bone and the surface of the implant. Because of the large stiffness difference, shear movements result along the interface between the surface of the implant and the adjacent surrounding bone tissue. Such shear movements cause the adjacent bony tissue to transform into soft tissue in a manner similar to the formation of a pseudarthrosis seam as often seen in insufficiently stabilized fracture sites. As such seams are known to increase the probability of a progressive loosening of the implant leading to eventual removal of the implant, the avoidance of the formation of such soft tissue interlayers has become the generally adopted aim. Instead, one tries to achieve and maintain a close bone contact along all interfaces available for load transmission.

Since the differences of the stiffnesses of bone and implant had been regarded as one of the main causes for implant failures, it had been suggested to adjust the stiffness of such implants to that of the surrounding tissue. However, the clinical applications of such "isoelastic implants" have not resulted in improved success rates.

These known isoelastic implants carried means for load transmission to and from the surrounding tissue along all the surfaces of their anchoring portions. Immediately after insertion, however, different portions of the implant are in contact with differently structured bony tissue with different interfacial conditions of load transfer. Thus, the remodelling of the bony tissue will progress differently at different locations of the interface. If for example, because of some locally particularly favorable conditions, the interfacial remodelling leads to the formation of a well load transmitting bond along the middle of the anchoring portion of the implant, one of the remaining parts (the "downstream" or distal one if looked at from the direction of the applied load) will remain unloaded and, thus, not deform with the tissue adjacent to it. This, in turn, would allow for interfacial motion with all the detrimental effects discussed above. It would defeat the intended function of the isoelastic implant.

If isoelastic implants are to perform their intended function, a way must be found to provide for reliable bone contact with the isoelastic implant along all of the interfaces essential for load transmission.

OBJECTS AND SUMMARY OF THE INVENTION

It is a principal object of the present invention to provide an isoelastic implant that reliably contacts bone along only the interfaces essential for load transmission.

It is another principal object of the present invention to provide an isoelastic implant that has anchorage means to foster reliable contact with bone along only the interfaces essential for load transmission.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the device of the present invention comprises an implant member defining an anchoring portion. The inventors realize that some medical conventions use the terms proximal and distal to mean closer to or farther away from the center of the body. However, for the purpose of this description of the present invention only, the direction of the load applied by the implant member to the bone establishes the proximal and distal ends of the implant member. The proximal end is the end of the implant closer to the site where the implant enters the bone, and the distal end is farthest from the site where the implant enters the bone tissue in question. According to the invention, the anchoring portion is provided with means of attachment to and load transfer from the surface of the anchoring portion into the inner surface of the bone along only two regions of the anchoring portion. One of these two regions is designated the proximal attachment and load transfer region or simply the proximal region. The other of these two regions is designated the distal attachment and load transfer region or as simply the distal region. Examples of the location of each of the two regions are provided in the detailed description which follows, and examples are provided for both femoral and acetabular implant configurations.

The means of load transfer and bone attachment within these proximal and distal regions can be any kind of surface structure providing for a mechanical interlocking and/or any kind of surface modification allowing for bond formation between the shaft and the bony tissue. Examples of surface structures in a configuration suitable for the load transfer and attachment means according to the present invention include undulations, gaps, protrusions, holes, grooves, pores, or lacunae. These structures can be formed from porous coatings, bioactive coatings, and a particular surface roughness that has a microscopic attachment configuration.

The location and size of each proximal region and distal region can be determined mathematically from parameters as described in the detailed description below. One parameter is the load bearing ability per unit of surface area of the means of attachment and load transmission that occupies the proximal and distal regions for the implant in question. Another parameter is the body weight of the person for which the particular implant is intended to be used. Desirably at least half, but not more than 90%, of the total load must be transferred via the proximal portion of the anchoring portion. Thus, the size of the proximal load bearing region must always be larger than that of distal load bearing region provided they have means of attachment and load transmission of equal ability. Thus, one must take into account the fact that one surface structure might be more effective in forming the desired bond than another surface structure.

The accompanying drawings, which are incorporated in and constitute a part of this specification, illustrate one embodiment of the invention and, together with the description, serve to explain the principles of the invention.

Figure 5:
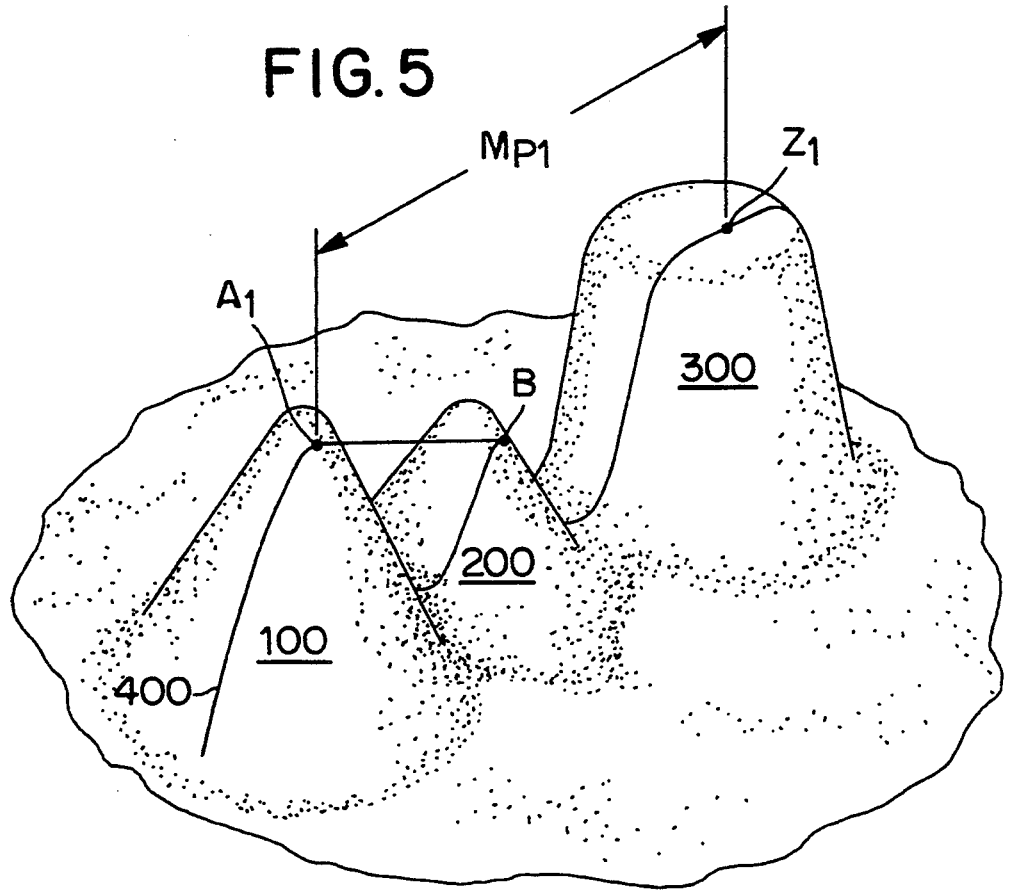
FIG. 5 is a schematic illustration of a partial, enlarged perspective view of an attachment configuration of the roughness band portion of an embodiment of the present invention.

Each of FIGS. 6-9 is a graphical representation of the profilometer path 400 followed in the embodiment shown in FIG. 5 and is intended to illustrate schematically various important dimensions of the attachment configuration of this embodiment of the present invention; and Each of FIGS. 10-14 is an elevated perspective view of a section of the surface of an embodiment of the implant of the present invention in one of the load transfer regions.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numbers are used consistently throughout the different Figs. to designate the same features.

Figure 1:
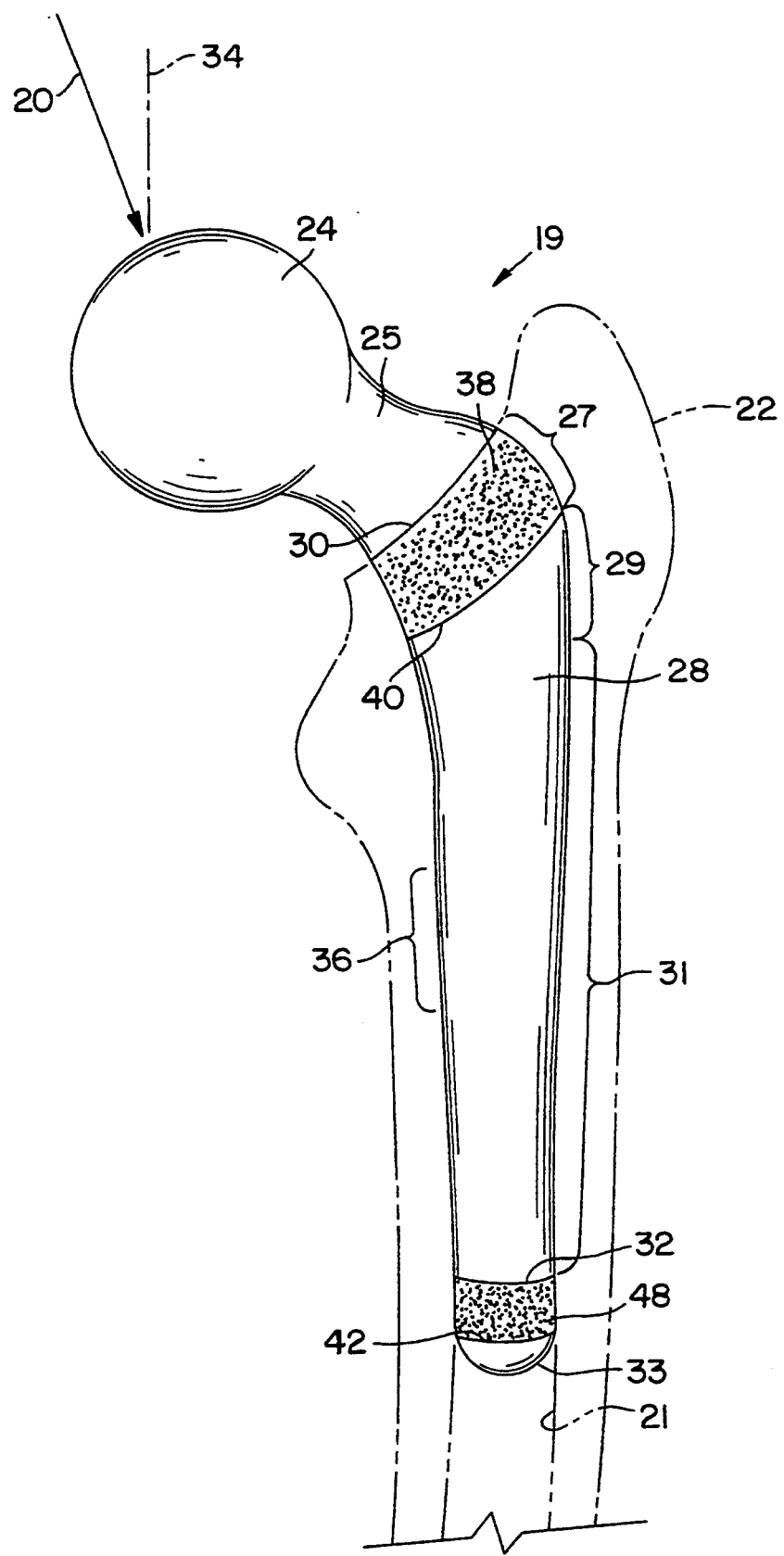
FIG. 1 illustrates a perspective side view of the femoral component of a total hip replacement according to a preferred embodiment of the present invention inside a femur shown in phantom by the dashed line outline.
Figure 2:
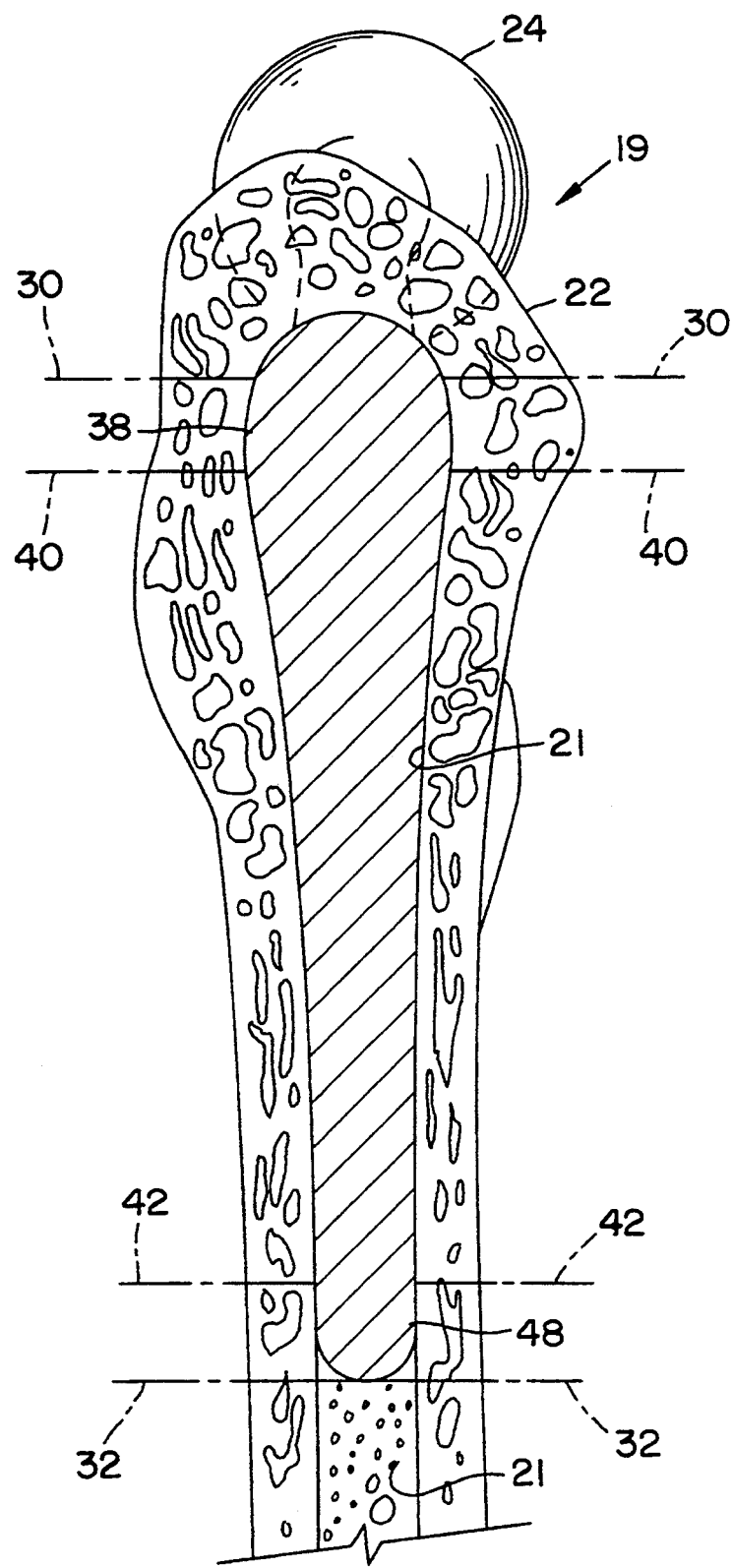
FIG. 2 illustrates a perspective back view and partial cross-sectional view of the femoral component of a total hip replacement according to a preferred embodiment of the present invention inside a femur shown in partial cross-section.

FIGS. 1 and 2 show an implant member in the form of the femoral component (indicated by a solid line and generally designated by the number 19) of a total hip replacement embedded into the femur 22 (indicated in FIG. 1 by the dashed line 22). Femur 22 has been prepared in a conventional manner with an elongated internal cavity defined by an interior wall 21 of the bone in order to receive implant 19. The shaft 28 of this femoral component 19 can be regarded as one extreme of a linearly extending anchoring portion (extending between circumferential lines designated 30 and 42). The load to be transmitted to the implant is applied essentially parallel to the longitudinal axis of shaft 28. As shown in FIG. 1 for example, the direction of such load is indicated by the arrow designated 20, and the major component of load 20 is applied in the direction indicated by the dashed line designated 34. The direction of line 34 is essentially parallel to the longitudinal axis of shaft 28.

A ball shaped head section 24 disposed at one end (the proximal end) of the femoral component 19 would be inserted into the socket component which is partially shown in FIG. 3 and generally designated by the numerical 26 for example. According to the state of the art, the head 24 will either be made of a metal or a ceramic material suitable for providing the properties required for the articulating engagement with socket 26. The head will be fixed to the neck portion 25 of the femoral component 19 according to the state of the art, as for example via a conical sleeve such as a so-called "Morse cone."

Shaft 28 is the anchoring portion of femoral component 19 and extends from just below neck portion 25 to a distal tip 33. The end of the neck 25 and the beginning of shaft 28 is indicated by the line 30 in FIG. 1. Line 30 is positioned to coincide with the level to which such a (collarless) implant is inserted into the femur, the contour of which is indicated by the dashed line 22 in FIG. 1. This level is identical with and results from the intraoperational resection of the head from the rest of the femur. It is the purpose of shaft 28 to transmit the load 20 (and in particular its component which is exerted in the direction indicated in FIG. 1 by the dashed line designated 34 and oriented parallel to the main axis of shaft 28) from the implant 19 into the femur 22.

According to the invention, shaft 28 is provided with means of attachment to and load transfer from the surface of shaft 28 into the inner surface of the femur 22 along only two regions of the shaft 28. One of these two regions is designated 38 and extends around the surface of shaft 28 between the circumferentially extending closed lines designated 30 and 40. The attachment and load transfer region 38 is also referred to as the proximal attachment and load transfer region or simply the proximal region, and in FIG. 1 for example is further indicated by the pointed parenthesis designated with the number 27. The other of these two regions is designated 48, and extends around the surface of shaft 28 between the circumferentially extending closed lines designated 32 and 42. The attachment and load transfer region 48 is also referred to as the distal attachment and load transfer region or as simply the distal region. Line 42, which defines the distal-most boundary of distal region 48, is the line where distal tip 33 of shaft 28 diverges out of contact with interior surface 21 of the cavity of femur 22. The remaining surfaces of shaft 28 are left without any means of bonding or otherwise allowing load transfer.

The means of load transfer and bone attachment within these proximal and distal regions (such as 38 and 48) can be any kind of surface structure providing for a mechanical interlocking and/or any kind of surface modification allowing for bond formation between the shaft and the bony tissue. Examples of surface structures suitable for load transfer and attachment means includes undulations, grooves, pores, or lacunae. The presence of structures suitable for means of load transfer and bone attachment is schematically illustrated by the stippling in FIGS. 1, 3A and 3B for example.

According to the present invention, all surfaces other than the proximal and distal regions (such as 38 and 48) must remain free from any kind of surface structure which would provide for mechanical interlocking and/or any surface modification that would allow for load transfer. The reason for this requirement is the realization by the inventors that the advantages of the isoelastic (or rather the "iso-stiff") implant can be realized only if the site of the lead transfer from the implant into the surrounding bone and the amount of load transmitted at each location can be controlled with a high degree of precision. For example, if, for some particularly favorable local conditions, the remodelling of the bony tissue adjacent to the midshaft region indicated by the pointed parenthesis designated with the numeral 36 in FIG. 1 would result in faster formation of a load bearing bond than along the rest of the bone/implant interface, the rest of the shaft (further distal to the area 36) would remain unloaded and result in shear movements along the interfaces between the distal portion of the shaft (between the area 36 and the line 42 defining the beginning of distal tip 33) and the adjacent bone. In addition, the portions of the femur between the area 36 and the resection plane at level 30 would remain unloaded and, thus, suffer from disuse atrophy.

Since according to this invention, only the proximal region 38 and the distal region 48 of the surfaces of shaft 28 of implant 19 carry or contain means for bone attachment and load transmission, any relative motion between the shaft's surface located between these end portions (38 and 48) and the bony tissue adjacent to it can be excluded in accordance with the definition of isoelasticity (or, more precisely, equal stiffness).

The location and size of each proximal region 38 and distal region 48 can be determined as follows. The sum of the surface areas of shaft 28 occupied by the load transfer regions 38 and 48 can be determined mathematically from a couple of parameters. One parameter is the load bearing ability per unit of surface area of the means of attachment and load transmission that occupies regions 38 and 48 for the implant in question. The other parameter is the body weight of the person for which the particular implant is intended to be used. As each hip joint must carry a load amounting to up to four times the person's body weight, this area sum can be derived by dividing four times the person's body weight by the load bearing ability per unit of surface area of the means of load transfer chosen in a particular case. Experiments and previous clinical studies have shown that at least half, but not more than 90%, of the total load must be transferred via the proximal portion (region 38) of the shaft. Thus, the size of the proximal load bearing region 38 must always be larger than that of distal load bearing region 48 provided they have means of attachment and load transmission of equal ability. Thus, one must take into account the fact that one surface structure might be more effective in forming the desired bond than another surface structure.

Figure 3A:
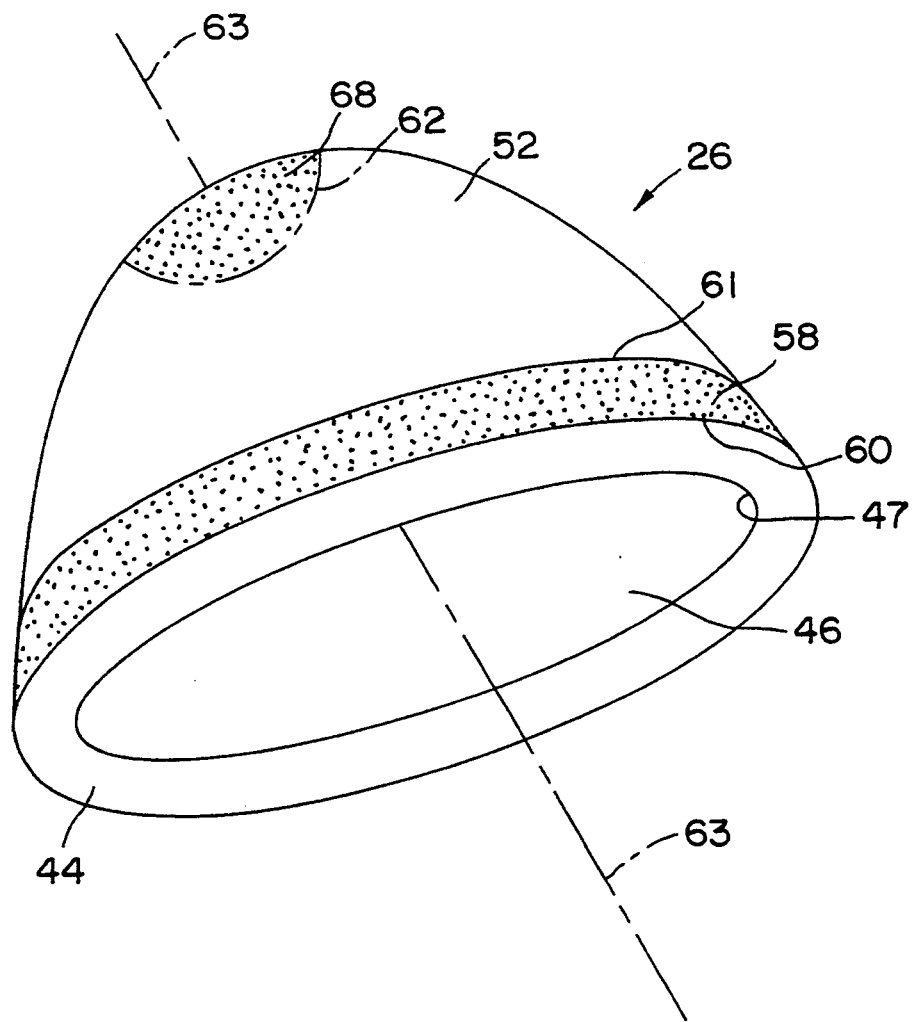
FIG. 3A schematically illustrates an elevated perspective view of an acetabular component (the socket) of a total hip replacement according to a preferred embodiment of the present invention.

FIG. 3A schematically shows an elevated perspective view of an implant member in the form of an acetabular component (the socket generally indicated by the numeral 26) of a total hip replacement in accordance with the present invention. The full main body 44 of this socket implant component 26 is assumed to be a hemispherical shell in overall configuration. The hollow space 46 defined by an inner wall surface 47 is intended to receive the ball (the artificial femoral head 24) of the femoral component 19. The outer surface (or layer if socket 26 is formed of two or more nested shells) of the socket 26 faces the bone (not shown) of the pelvis and defines the anchoring portion which carries or contains the means for bone attachment and load transmission only along the two separate regions 58 and 68.

Figure 3B:
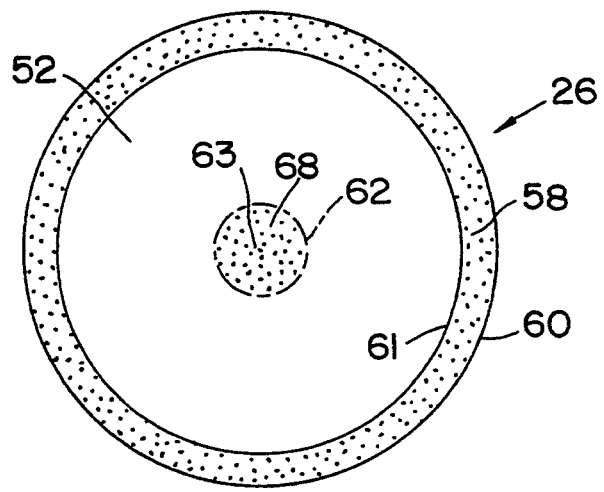
FIG. 3B schematically illustrates the top plan view of the acetabular component (the socket) of FIG. 3A looking down along the line of sight in the direction of central axis of revolution 63.
Figure 4:
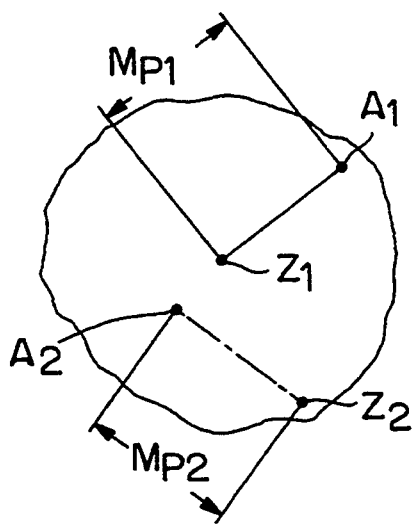
FIG. 4 schematically illustrates one method of choosing profilometer sampling paths that meet the sampling criteria for determining the roughness portion's attachment configuration according to the present invention.

As illustrated schematically in FIGS. 3A and 3B for example, the proximal attachment and load transmission region 58 (also known as the equatorial region 58) is disposed completely circumferentially around main body 44. Proximal region 58 extends in a band defined between two parallel lines 60, 61 which are analogous to a pair of parallels of a globe. Circumferentially closed line 60 is the largest closed circumferential line (analogous to the equator of the hemisphere) of socket 26 and is coextensive with the free edge of socket 26. The free edge of socket 26 is configured to be coextensive with the surface of the pelvic bone (not shown), which bone presumably has been prepared by the surgeon in a conventional manner to receive socket 26. Circumferentially closed line 61, which defines the other boundary of proximal region 58, is analogous to a parallel disposed at a given latitude of the hemisphere toward a central axis of rotation 63.

The distal attachment and load transmission region 68 (also known as the polar region 68) of the outer surface of socket 26 is bounded by the circumferentially extending closed dashed line designated 62 in FIGS. 3A and 3B.

The size of these proximal and distal regions 58, 68, respectively, is to be determined as outlined above for the proximal and distal regions 38, 48, respectively, of the shaft. Proximal region 58 along the rim of the socket 26 corresponds to the proximal region 38, and the distal region 68 around the pole or central axis of revolution 63 of the socket 26 corresponds to the distal region 48 of the shaft 28. The same constraints for the absolute and relative area calculations between the proximal and distal regions apply to both the shaft 28 and the socket 26.

Moreover, the shape of the proximal regions such as those designated 38 and 58 and the shape of the distal regions such as those designated 48 and 68, need not be as regular as shown in the Figs. For example, one of the boundaries can be a curved or jagged line, and the regions (such as 38, 48, 58, and 68) may be completely interrupted along at least one part of its circumference around the surface of the implant member. Each such interruption would mean the absence of the means of bone attachment and load transmission according to the present invention.

In accordance with the present invention, the means of bone attachment and load transmission, which is to be provided within the regions (e.g. regions 38, 48, 58, 68) for which such means is desired pursuant to the present invention, desirably can consist of macroscopic surface structures like holes and/or pores with depths of between 0.1 to 5 mm and cross sectional dimensions of between 0.1 to 5 mm (lacunae like) and/or grooves of similar dimensions allowing for bone in growth and load transfer by mechanical interlocking. Such a mechanical interlocking can also be achieved via porous coatings.

The means for bone attachment and load transfer can also be realized in accordance with the present invention by bioactive coatings that allow for a bond formation between normally proliferating tissue and the material of the coating. Examples of such bioactive coating materials are hydroxylapatite ceramics and some calcium-phosphate-containing glass ceramics. The bonds these materials form with living bone have been shown to be able to transmit shear loads. All these bioactive coatings are part of the state of the art and can be applied by all methods well known to those skilled in the art to the regions of load transfer that are specified in accordance with the present invention.

Yet other embodiments of the means for bone attachment and load transfer achieving the load transmitting properties within the regions for which this is required according to this invention are described and explained using FIGS. 4-14. As embodied herein and shown in FIGS. 5-14 for example, each site 38, 48, 58, and 68 for bone attachment and load transmission comprises a particular surface roughness that has a microscopic attachment configuration.

In accordance with the present invention, the surface roughness in the portions of the implant surface intended for bone attachment and load transmission, has the attachment configuration of the present invention provided that for a statistically significant sample of nonparallel unidirectional profilometer sampling paths, each path having an orthogonal projection $M_p$ measuring at least one-tenth millimeter in length on a flat plane, each of the mean values of the parameters S, D, T and G as shown in FIGS. 6-9 for example, satisfy the range wherein: (1) the mean D value is larger than 0.5 micrometers, (2) each of the mean values of G and T is from 0.5 to 5 micrometers, and (3) the mean S value is from 1 to 10 micrometers. In a particularly desirable embodiment of the attachment configuration, the mean value of the half-height widths G of the gaps and half-height thicknesses T of the protrusions is from 1 to 4 micrometers, the mean value of the depths D of the gaps is at least 0.5 micrometers, and the mean value of the spacings S between the adjacent protrusions is in the range from 1 to 4 micrometers.

A statistically significant sample would include measurements from at least 30 different noncoincident and nonparallel profilometer paths within a particular attachment and load transmission region 38, 48, or 58 formed in the surface of the bone implant of the present invention. Thus, as long as after 30 different straight line projections $M_P$ of 30 profilometer paths on the surface within an attachment and load transmission region 38, 48, or 58, no two of the 30 paths being coincident or parallel to each other, wherein the length of each of the projections $M_P$ measures at least one-tenth of a millimeter, the mean values of each of the parameters S, D, T and G fall within the designated ranges, then this surface has a roughness with the attachment configuration within the scope of the present invention. In other words, such a surface would have the particular kind of roughness specified according to the present invention.

Desirably, the measurements of each of the parameters S, D, T and G can be obtained using a surface profilometer. Brown & Sharpe of 27300 Haggerty Road, Farmington Hills, Mich. 48331 produces a line of SURFCOM surface profilometer instruments and the HANDY SURF E10 profilometer. Tencor Instruments of 2400 Charleston Road, Mountainview, Calif. 94043 produces the TENCOR P-1 LONG SCAN PROFILER surface profilometer. The profilometer maps the contour of a surface along the path over which the detecting probe of the profilometer moves. Typically, the profilometer permits the operator to select the cut-off length, which corresponds exactly to the sampling distance $M_P$. The measurements needed for the protrusion spacing (S), protrusion thickness (T), gap depth (D), and gap width (G) parameters can be obtained from the graphs generated by the profilometer. Then these graphs can be used to measure each of these parameters, and mean values can be calculated for the 30 sample path measurements.

The first parameter to be defined is the manner of measuring the sampling distance $M_p$, which as noted above is sometimes referred to in the profilometer art as the "cut-off length." Typically, a point will be selected as the starting point used in tracing the detection probe of the profilometer on the lens surface to be sampled within the attachment configuration. FIG. 5 schematically depicts a perspective view of an enlargement of a section within one of attachment and load transmission regions 38, 48, or 58 on the implant surface. However, in order to avoid obscuring certain features of the invention, all but three protrusions 100, 200, 300 have been omitted from the view shown in FIG. 5. As shown in FIG. 5 for example, a point "$A_1$" near the sharp peak of a protrusion 100 has been chosen arbitrarily as the starting point for tracing a path with the detection probe (not shown) of the profilometer. As shown in FIG. 5 for example, the projection $M_{P1}$ of the profilometer sampling path defined by a line $A_1$-$Z_1$ is the line $A_1$-$Z_1$ projected onto a flat plane. Thus, the line $A_1$-$Z_1$ represents the straight line path taken by the detection probe of the profilometer from point $A_1$, which is at the relative peak (the highest point in that immediate locality) of the protrusion 100, to point $Z_1$, which in FIG. 5 happens to be near the middle of a flat-topped protrusion 300. When the profilometer detection probe (not shown) is used to map the contour of the sampling path $A_1$-$Z_1$, the profilometer can generate in two-dimensional graphical format, a line representation 400 such as shown in FIGS. 5-9 for example. Once this graphical format has been obtained, then the remaining parameters of interest, namely, S, D, T, and G, can be measured and recorded for this particular profilometer path $A_1$-$Z_1$.

Figure 6:
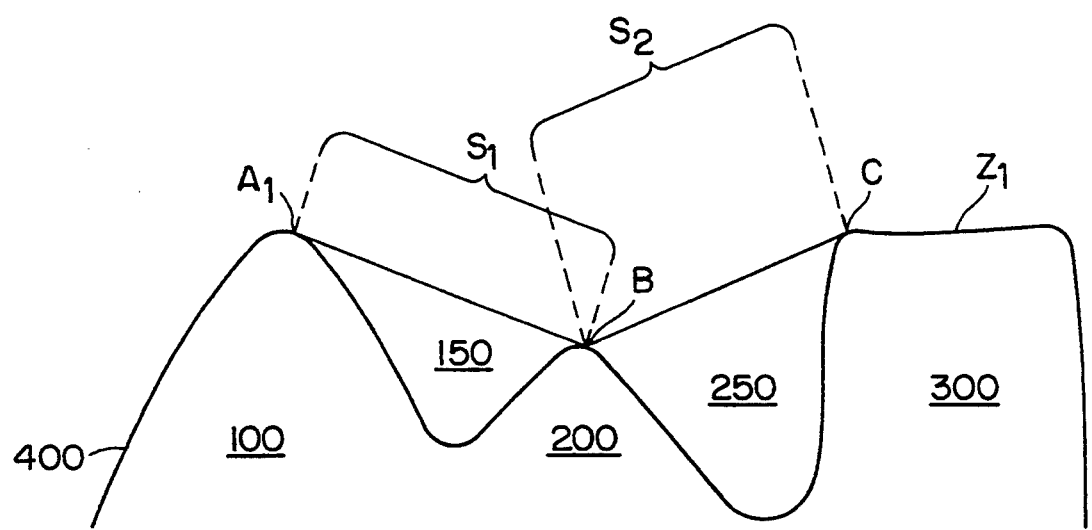

The first parameter is the so-called peak-to-peak spacing distance between adjacent protrusions (such as protrusions 100, 200 for example) in the sampling path and is represented by the letter S. This "peak-to-peak" description is only a precisely literal description when the direction of the path of the profilometer's sampling probe has been chosen so as to intersect the maximum points of two adjacent protrusions. Thus, another way of describing this protrusion spacing parameter S is the distance between the highest points on two adjacent protrusions in the path of the profilometer's sampling probe. As shown in FIG. 5 for example, the sampling probe path extends in a constant direction from point $A_1$ to point $Z_1$ and thus yields a straight line for the projection $M_{P1}$ of the path $A_1$-$Z_1$ onto a flat plane. Accordingly, as shown in FIG. 6 for example, at one end point $A_1$ of the straight line $A_1$-B which defines the spacing distance $S_1$, the protrusion 100 has been intersected at its highest point in the imaginary vertically extending plane (not shown) containing both the projection $M_{P1}$ and the sampling path $A_1$-$Z_1$. Similarly, the opposite end point B of the straight line $A_1$-B which defines the spacing distance $S_1$ is the localized highest point on the protrusion 200 residing in the same imaginary vertical plane (not shown) containing both the projection $M_{P1}$ and the sampling path $A_1$-B. As can be seen from FIGS. 5 and 6 for example, if the spacing line $A_1$-B were elevated above point B while still remaining in the same imaginary vertical plane (not shown) containing both the projection $M_{P1}$ and the sampling path $A_1$-$Z_1$, then the spacing line $A_1$-B no longer would be touching the surface of the smaller protrusion 200. In addition, if the spacing line $A_1$-B were lowered beneath point B while still remaining in the same imaginary plane, then the spacing line $A_1$-B would not be touching the highest point residing on the smaller protrusion 200 in the imaginary vertical plane including the projection $M_{P1}$ of the sampling path $A_1$-$Z_1$.

The first sampling path $A_1$-$Z_1$ shown in FIGS. 5 and 6 contains a second gap 250 between two adjacent protrusions 200, 300. Accordingly, a second spacing measurement $S_2$ will be taken. One end point B of the straight line B-C defining the $S_2$ spacing measurement is identical to the end point B of the first straight line $A_1$-B defining the first spacing measurement $S_1$. The opposite end point C of the straight line B-C defining the $S_2$ spacing measurement is once again where the surface of the adjacent protrusion 300 intersects the imaginary vertically extending plane containing both the projection $M_{P1}$ and the sampling path $A_1$-$Z_1$ followed by the profilometer.

Figure 7:
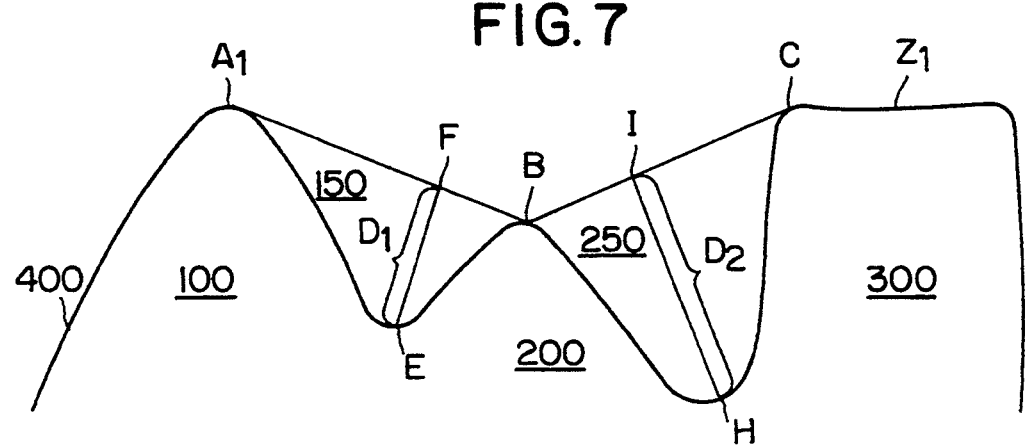

The second parameter to be measured from the graphical representation of the path taken by the profilometer probe is the depth measurement D of each gap encountered by the profilometer sampling probe as it follows the sampling path characterized by the projection $M_p$. As shown in FIG. 7 for example, the depth $D_1$ is defined by a line having one end point E at the bottom of the gap 150 and the opposite end point F at the perpendicular intersection with the straight line $A_1$-B that defines the corresponding spacing distance $S_1$ that bridges gap 150. Similarly, since there is a second gap 250 in this sampling path $A_1$-$Z_1$, a second depth measurement $D_2$ is obtained in a similar fashion. One end point H of the $D_2$ depth measurement is the bottom of the second gap 250, and the opposite end point I is the normal intersection of the associated spacing line B-C which measures spacing distance $S_2$ that bridges second gap 250. Thus, there are two depth measurements $D_1$ and $D_2$ along this particular sampling path $A_1$-$Z_1$ with its projection measuring $M_{P1}$.

Figure 8:
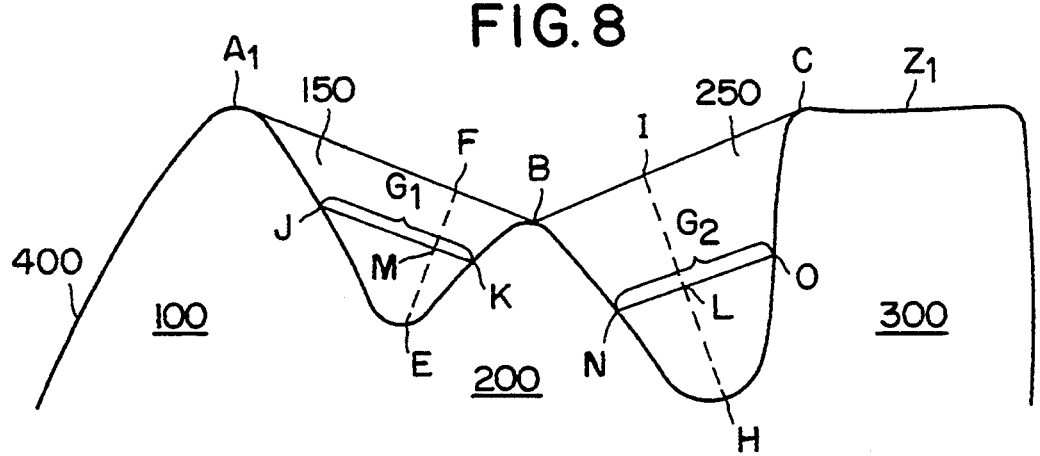

The third parameter is the gap width G of each gap 150, 250. As shown in FIG. 8 for example, the gap width measurement $G_1$ is obtained by locating the two end points of the straight line which defines the gap width $G_1$ measurement. This line defining the gap width distance $G_1$ is parallel to the spacing line A-B defining the spacing measurement $S_1$ and resides in the same plane as the spacing line $A_1$-B and as the projection $M_{P1}$ of the sampling path $A_1$-$Z_1$. The gap width measuring line is therefore also oriented so as to be perpendicular to the depth measuring line E-F (shown dashed in FIG. 8) defining the gap depth measurement $D_1$. The gap width measuring line intersects the depth measuring line E-F at the midpoint M of the line E-F which defines the gap depth measurement $D_1$. This is why the gap width measurement is sometimes referred to as the "gap half height width measurement." The end points J and K of the gap width measuring line J-K are determined by the intersection of the gap width measuring line J-K with the opposed surfaces of the side walls of the adjacent protrusions 100, 200 which define the first gap 150. The length of the gap width line J-K equals the gap width measurement $G_1$.

As shown in FIG. 8, there is a second gap 250 encountered by the detecting probe of the profilometer as the profilometer travels to define the sampling path $A_1$-$Z_1$. The gap width measurement $G_2$ of the second gap 250 is obtained in the same fashion as the gap width measurement $G_1$ of the first gap 150. The second gap width line is oriented by perpendicularly intersecting the midpoint L of the second gap depth line H-I. The end points N and 0 of the second gap width measuring line N-0 are determined by the intersection of the gap width measuring line N-0 with the opposed surfaces of the side walls of the adjacent protrusions 200, 300 which define the second gap 250. The length of the second gap width line N-0 equals the gap width measurement $G_2$.

Figure 9:
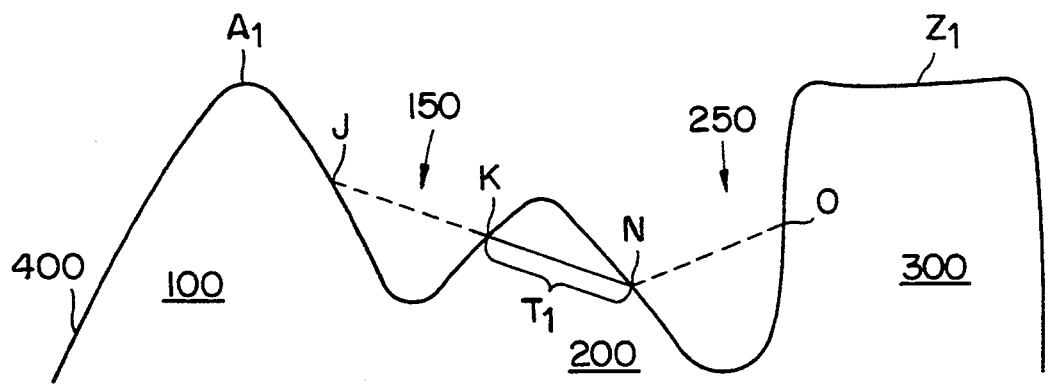
Figure 10:
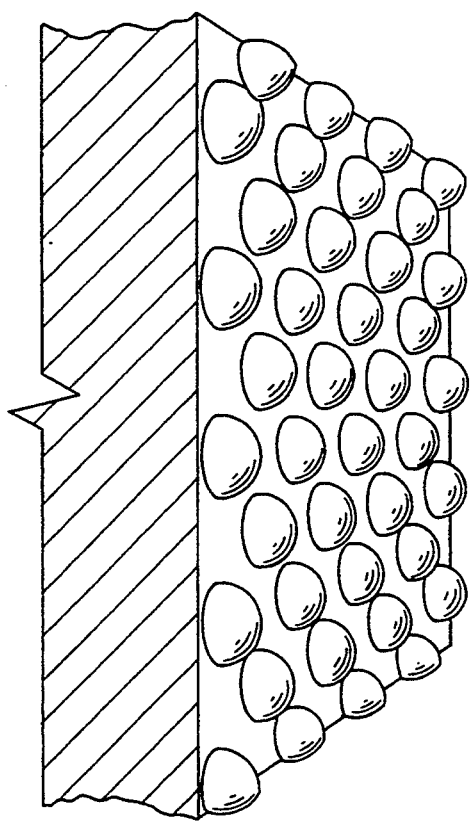

The fourth and final parameter is the thickness T of each protrusion that is wholly encompassed within the sampling path of the detecting probe of the profilometer. Only one such protrusion 200 satisfies this definition in the sampling path $A_1$-$Z_1$ shown in FIGS. 5 and 9. As shown in FIG. 9 for example, the protrusion thickness measurement $T_1$ is obtained by measuring the length of the straight line K-N, which extends between the point K where the first gap width line J-K intersects the surface of the protrusion 200 on one end of line K-N and the point N where the second gap width line N-0 defining the second gap width measurement $G_2$ of the second gap 250 intersects the surface of the protrusion 200 on the other end of protrusion thickness line K-N. Since K and N are both endpoints of their respective half gap width lines K-J and N-0, the thickness measurement T is sometimes referred to as the half-height thickness measurement.

In order to obtain the mean values of each of the four parameters, an additional 29 sample paths ($A_2$-$Z_2$, $A_3$-$Z_3$, $A_4$-$Z_4$, * * * and $A_{30}$-$Z_{30}$) must be traced by the profilometer to yield a total of 30 profilometer sampling paths. More than 30 sampling paths can be used, but at least 30 profilometer sampling paths should be used in order to assure statistical accuracy. Each of the corresponding additional profilometer projections ($M_{P2}$, $M_{P3}$, $M_{P4}$, * * * and $M_{P30}$) must measure at least one-tenth of a millimeter. The additional profilometer projections ($M_{P2}$, $M_{P3}$, $M_{P4}$, * * * and $M_{P30}$) beyond the first profilometer projection $M_{P1}$ can be generated in a methodical fashion. To generate the additional 29 sample paths for taking the measures of the required parameters S, D, G, and T, one need only select another starting point $A_i$ and ending point $Z_i$ so that the line $A_i$-$Z_i$ has a projection $M_{Pi}$ therebetween, wherein the projection $M_{Pi}$ is neither coincident nor parallel to the projection of any other sampling path. As shown schematically in FIG. 4 for example, the projection $M_{P2}$ of sampling path $A_2$-$Z_2$ is neither coincident nor parallel to the projection $M_{Pi}$ of sampling path $A_1$-$Z_1$, nor would it be to any other projection $M_{Pi}$ of any other sampling path $A_i$-$Z_i$.

Once all of the calculations of each of the four parameters S, D, G, and T, are obtained in the manner described above, the mean value of each parameter is obtained as follows. Each of the calculated values of a given parameter (either S or D or G or T) is added together to yield a sum which is divided by the number of such values which were measured during the 30 sampling path movements of the profilometer. For a hypothetical example in which the 30 sampling movements of the profilometer produces 56 protrusion spacing measurements S, then each of these 56 spacing measurements are added together to obtain a sum of the 56 spacing distances ($S_1 + S_2 + S_3 +$ * * * $+S_{56} = SUM_{56}$). Then this sum of the values for all of the spacing measurements for the 30 sampling paths of the profilometer is divided by the number (56 or in general terms "n") of spacing measurements to yield the arithmetic mean value of the spacing distance in the region of the attachment and load transmission region 38, 48, or 58 in which the measurements were taken.

$$S_{mean} = \frac{1}{n} \sum_{i=1}^{i=n} S_i$$

Once each of the mean values for each of the parameters is calculated, then each of these mean values is examined to determine whether it falls within the ranges that are required for the attachment configuration according to the present invention. In particular, the so-called peak-to-peak spacings (S) between adjacent protrusions must have a mean value of 1 to 10 $\mu$m. The depth (D) of the gaps must have a mean value of at least 0.5 $\mu$m. The so-called half-height width (G) of the gaps must have a mean value of between 0.5 to 5 $\mu$m. The so-called half-height thickness (T) of the protrusions must have a mean value of between 0.5 and 5 $\mu$m.

The embodiments of the attachment configuration of the roughness of the present invention shown in FIGS. 10-14 for example, are regularly repeating patterns. Such regular attachment configuration patterns may be obtained in accordance with the method disclosed at columns 11-12 in particular of U.S. Pat. No. 5,011,494, which patent is hereby incorporated herein by this reference.

Figure 11:
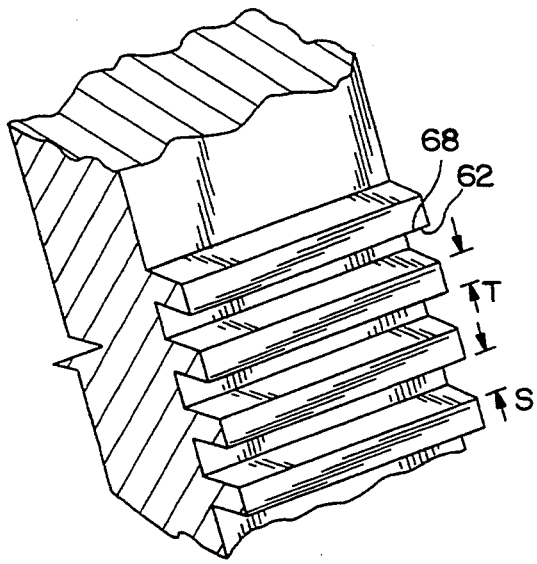
Figure 12:
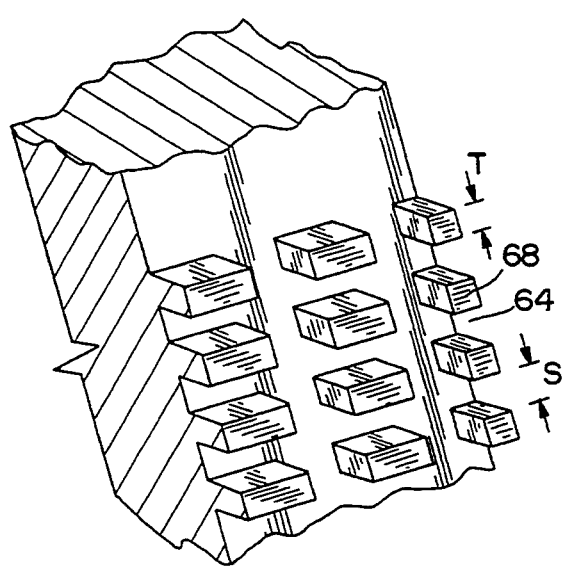
Figure 13:
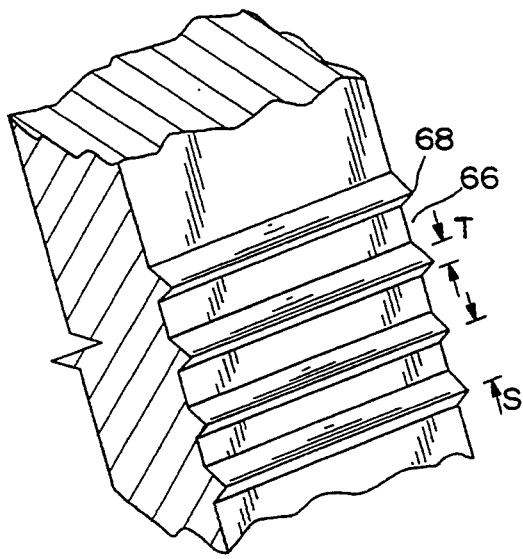

As shown in FIGS. 11, 12 and 13 for example, some embodiments of the attachment configuration include grooves 62, 64, or 66, respectfully, disposed to extend circumferentially about the longitudinal axis (not shown) of the implant shaft with the mean value of the depths of said grooves in the range of from 1 to 4 micrometers, with the mean value of the half-height thicknesses T of the surface portion 68 between adjacent ones of grooves 62, 64, or 66 in the range of from 1 to 4 micrometers, and with the mean value of the peak-to-peak spacings S across each groove 62, 64, and 66 in the range of from 1 to 5 micrometers. Thus, the attachment configuration can have a more ordered structure so long as the basic parameters meet the specified mean values. Both the degree of uniformity and the sizes of grooves 62, 64, and 66 and intermediate surface portions 68 in FIGS. 11, 12 and 13 have been exaggerated to a higher degree of uniformity and larger than scale in order to facilitate illustration of these embodiments.

Figure 14:
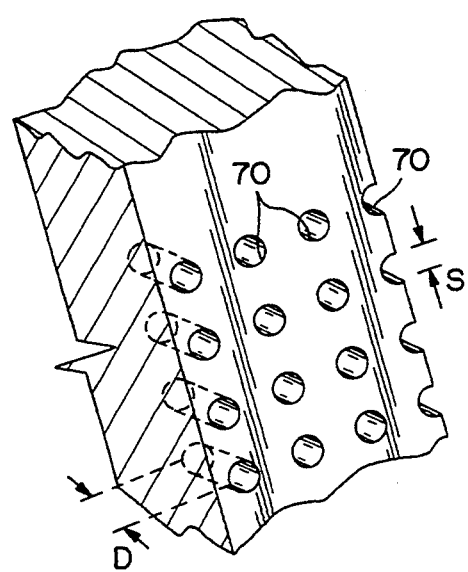

As shown in FIG. 14 for example, an alternative preferred embodiment of the attachment configuration of the present invention includes holes 70 with depths D of between 0.1 millimeters ($10^{-3}$ meters) to 3 millimeters and cross-sectional dimensions S of between 0.1 millimeters to 5 millimeters (lacunae like) allowing for bone in growth and load transfer by mechanically interlocking the bone into the holes of the implant's surface. Such a mechanical interlocking can also be achieved via porous coatings in which the dimensions of the surface openings are 0.1 millimeter to 5 millimeters.

Of course, more than one embodiment of the means for attachment and load transfer can be combined with another embodiment of the means for attachment and load transfer, provided that they can be matched for commensurate rates of attachment.

What is claimed is:

1. A device implantable without bone cement and for replacing joints of load bearing bones in living tissue of mammals, the device comprising:
   a) a first implant member, said first implant member defining an anchoring portion formed of isoelastic material, said anchoring portion having proximal and distal ends and a central portion separating said proximal and distal ends and extending continuously therebetween, said anchoring portion having an imaginary midline dividing said anchoring portion substantially in half, said first implant member further defining:
i) a first surface region located at said proximal end,
ii) a second surface region located at said distal end and disposed only distally of said imaginary midline, and
iii) means for attachment and load transmission between said anchoring portion and the surrounding tissue, said attachment and load transmission means being disposed solely within said first and second surface regions and wherein said central portion being devoid of any surface which provides mechanical interlock with and load transfer to the surrounding tissue.

2. A device as in claim 1, wherein said first surface region and said attachment and load transmission means are configured to transfer from 50% to 90% of the total load to be carried by said first implant member to the surrounding tissue.

3. A device as in claim 1, wherein said first implant member is configured as a femoral component of a hip replacement and includes:
a) an elongated shaft defining said anchoring portion, a neck portion connected to said proximal end of said shaft, and a head portion connected to said neck portion.

4. A device as in claim 3, wherein said shaft defines a distal tip and said second region defines a distal-most boundary, and wherein said distal-most boundary of said second surface region begins substantially where said distal tip begins contact with the surrounding tissue.

5. A device as in claim 1, wherein said attachment and load transmission means is configured for mechanically interlocking directly with the surrounding tissue.

6. A device as in claim 1, wherein said attachment and load transmission means includes macroscopic grooves.

7. A device as in claim 1, wherein said attachment and load transmission means includes lacunae.

8. A device as in claim 1, wherein said attachment and load transmission means includes porous coatings.

9. A device as in claim 1, wherein said attachment and load transmission means is configured to provide for direct mechanical interlocking attachment of bony tissue able to transmit shear forces.

10. A device as in claim 1, wherein said attachment and load transmission means includes bioactive coatings.

11. A device as in claim 1, wherein said attachment and load transmission means includes periodic surface undulations with depths in the range of 0.1 to 5 micrometers and repeating distances of between 1 to 3 micrometers.

12. A device as in claim 1, wherein said attachment and load transmission means includes an attachment configuration defining a plurality of gaps and protrusions.

13. A device as in claim 12, wherein the mean value of the widths of said gaps is from 1 to 4 micrometers, the mean value of the thicknesses of said protrusions is from 1 to 4 micrometers, the mean value of the depths of said gaps is at least 0.5 micrometers, and the mean value of the spacings between said gaps is in the range from 1 to 4 micrometers.

14. A device as in claim 12, wherein said attachment configuration includes circular grooves disposed about the longitudinal axis of said implant member and with the mean value of the depths of said grooves in the range of from 1 to 4 micrometers, with the mean value of the half-thicknesses of the surface portion between adjacent ones of said grooves measured in the longitudinal direction in the range of from 1 to 4 micrometers, and with the mean value of the peak-to-peak spacings between adjacent grooves measured in the longitudinal direction in the range of from 1 to 5 micrometers.

15. An implantable device for replacing joints of load bearing bones in living tissue of mammals, the device comprising:
a) a first implant member, said first implant member defining an anchoring portion formed of material having a stiffness substantially matching that of the bone, said anchoring portion having proximal and distal ends and a central portion separating said proximal and distal ends, said first implant member further defining:
i) a first surface region located at said proximal end,
ii) a second surface region located at said distal end,
iii) means for attachment and load transmission between said anchoring portion and the surrounding tissue, said attachment and load transmission means being disposed solely within said first and second surface region and wherein said central portion having a surface which prevents mechanical interlock with and load transfer to the surrounding tissue, and
wherein said first implant member is configured in the form of an acetabular component for receiving a ball of a femoral component and defines:
iv) a main body defining a hemispherical cavity configured for receiving the ball of the femoral component and allowing articulating movement between the ball and said cavity, said main body defining an outer surface having a free edge; and
v) wherein said first surface region is formed on said outer surface and extends from said free edge of said main body.

16. A device as in claim 15, further comprising:
b) a second implant member, said second implant member defining a second anchoring portion formed of material having a stiffness substantially matching that of the bone, said second anchoring portion having proximal and distal ends and a central portion separating said proximal and distal ends, said second implant member further defining:
i) a first surface region of said second anchoring portion located at said proximal end of said second anchoring portion,
ii) a second surface region of said second anchoring portion located at said distal end of said second anchoring portion, and
iii) a second means for attachment and load transmission between said second anchoring portion and the tissue surrounding said second anchoring portion, said second attachment and load transmission means being disposed solely within said first and second surface regions of said second anchoring portion and wherein said central portion of said second anchoring portion having a surface which prevents mechanical interlock with and load transfer to the surrounding tissue;
c) wherein said second implant member is configured as a femoral component of a hip replacement and includes:
i) an elongated shaft defining said second anchoring portion, a neck portion connected to said proximal end of said shaft, and a head portion connected to said neck portion.

* * * * *